United States Patent [19]

Wickham et al.

[11] 3,964,473

[45] June 22, 1976

[54] BONE PROSTHESIS

[75] Inventors: Geoffrey Gordon Wickham; Allen Frederick Dwyer, both of Sydney, Australia

[73] Assignee: Telectronics Pty. Limited, New South Wales, Australia

[22] Filed: Sept. 19, 1973

[21] Appl. No.: 398,880

[30] Foreign Application Priority Data
Sept. 21, 1972 Australia.............................. 516/72

[52] U.S. Cl. ............................ 128/82.1; 128/419 F; 3/1.913
[51] Int. Cl.² ........................ A61N 1/00; A61F 1/04
[58] Field of Search ........... 128/82.1, 419 R, 419 F, 128/419 P, 418, 416, 411, 410, 405, 404, 92; 3/1

[56] References Cited
UNITED STATES PATENTS

| | | | |
|---|---|---|---|
| 2,719,522 | 10/1955 | Hudack | 128/92 |
| 2,765,787 | 10/1956 | Pellet | 128/92 |
| 3,737,579 | 6/1973 | Bolduc | 128/419 P |
| 3,745,995 | 7/1973 | Kraus | 128/82.1 |
| 3,749,101 | 7/1973 | Williamson | 128/418 |
| 3,788,329 | 1/1974 | Friedman | 128/418 |
| 3,820,534 | 6/1974 | Kraus et al. | 128/82.1 |
| 3,842,841 | 10/1974 | Brighton et al. | 128/419 R |

*Primary Examiner*—John D. Yasko
*Attorney, Agent, or Firm*—Flehr, Hohbach, Test, Albritton & Herbert

[57] ABSTRACT

The disclosure relates to a bone prosthesis having a keying electrode. The electrode is provided with key formations into which bone may grow for locking engagement therewith.

2 Claims, 7 Drawing Figures

BONE PROSTHESIS

This invention relates to the affixture of prostheses to living bone.

Hitherto prostheses have been secured to bone, by a variety of mechanical arrangements by an acrylic cement.

The cement produces distressing tissue reaction in some people; it is also subject to an elevated exothermic temperature during curing and is prone to long term degeneration due to water absorption.

The invention provides a prosthesis adapted to be secured to the bone by growth of the bone into interstices or recesses in the prosthesis under the influence of a growth stimulating electric potential.

According to the invention a bone prosthesis is provided comprising a core, a keying electrode covering part of the core and an insulating layer sandwiched between the core and electrode securing each to each; said electrode being shaped or surface conditioned to provide key formations into which bone may grow for locking engagement therewith.

The electrode may be so shaped or conditioned by for example providing its surface with a plurality of recesses or projections, its surface may be imbricated or crenellated. The electrode may be a woven wire mesh or net. It may be shaped as an open ended tube extending through the core. It may be a perforated metal shell. In some cases it may suffice for the electrode merely to have a rough exterior surface.

According to preferred embodiments of the invention the core is a metallic body comprising an exposed joint portion adapted to co-operate with an undamaged bone and a shaft adapted to be inserted into a damaged bone. The shaft is coated with an insulating layer of polyvinyl chloride, polythene, nylon or teflon, keyed to the shaft by multiple serrations in the shaft, or perforations, fastening pegs or adhesive bonding.

Over the insulating material is attached a cathodic electrode in the form of a mesh or grid.

In use, polarisation of the cathodic electrode by means of an implantable electric stimulator such as that of our copending application Ser. No. 398,881, filed Sept. 19, 1973 for Bone Growth Stimulator, now abandoned, causes bone growth around and into the irregularities in the electrode.

By way of example two hip-joint prostheses according to the invention are described hereinafter with reference to the accompanying drawings.

Figure 1:
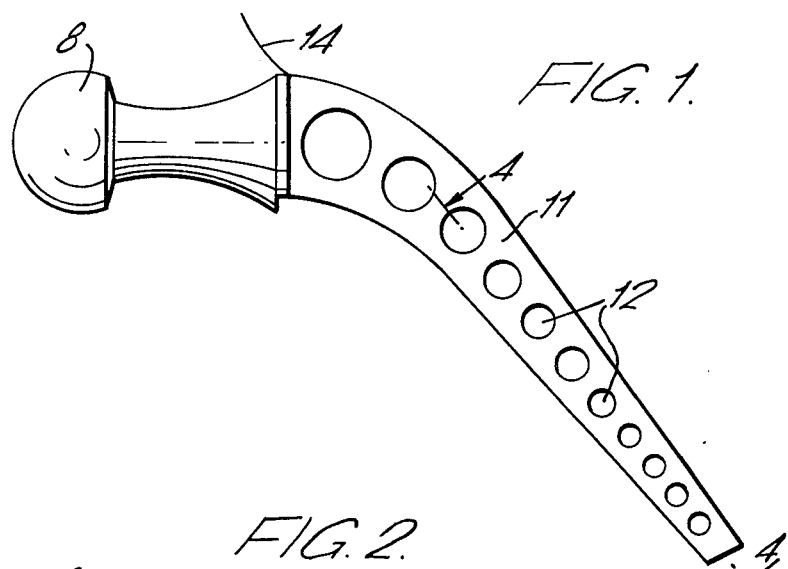
FIG. 1 is a side elevation of a hip joint prosthesis according to the invention.
Figure 2:
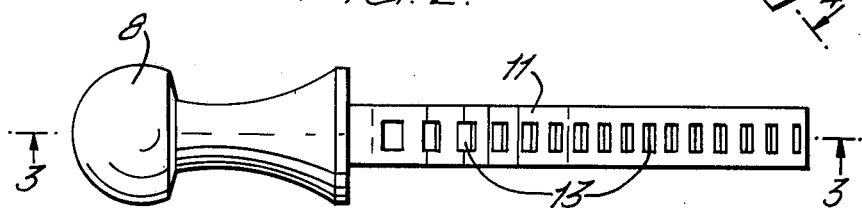
FIG. 2 is a plane view of the prosthesis of FIG. 1.
Figure 3:
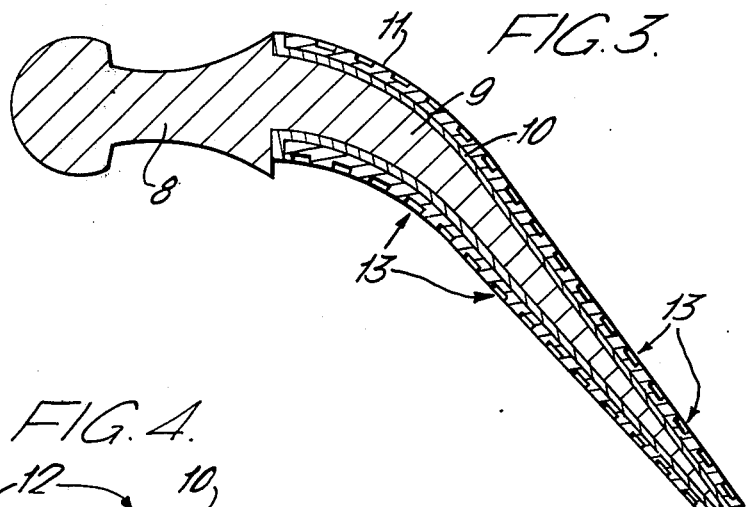
FIG. 3 is a sectional view taken on line 3—3 of FIG. 2.
Figure 4:
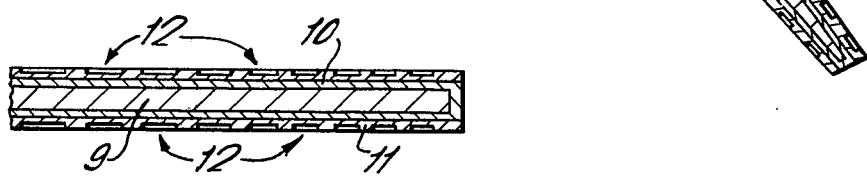
FIG. 4 is a sectional view taken on line 4—4 of FIG. 1.

The embodiment of the invention illustrated by FIGS. 1 to 4 includes a core of titanium or other inert metal or hard plastics material comprising a part-spherical head 8 adapted to co-act with a sound pelvic socket and a shaft 9 adapted to be inserted into the interior of a broken femur.

The shaft 9 is covered by an adherent layer 10 of polythene or other insulatory material, and that layer is itself shrouded by a cathodic electrode 11.

The electrode 11 has recesses 12 and 13 formed in it or is otherwise roughened, imbricated or recessed to provide a keying formation with bone growing from the femur.

Both the core and the electrode 11 may be titanium and are preferably made by a vacuum investment casting process.

The electrode 11 is preferably cast in two parts separated along the intersections of their plan and profile views. After assembly of the two parts of the electrode they are united by welding.

The electrode 11 may be then jigged into its correct position over the shaft 9 in an injection moulding die and the polythene or other insulant injected under heat and pressure into the interspace.

A lead 14 extends from the electrode 11 for its connection as a cathode to an electric bone growth stimulator.

Figure 5:
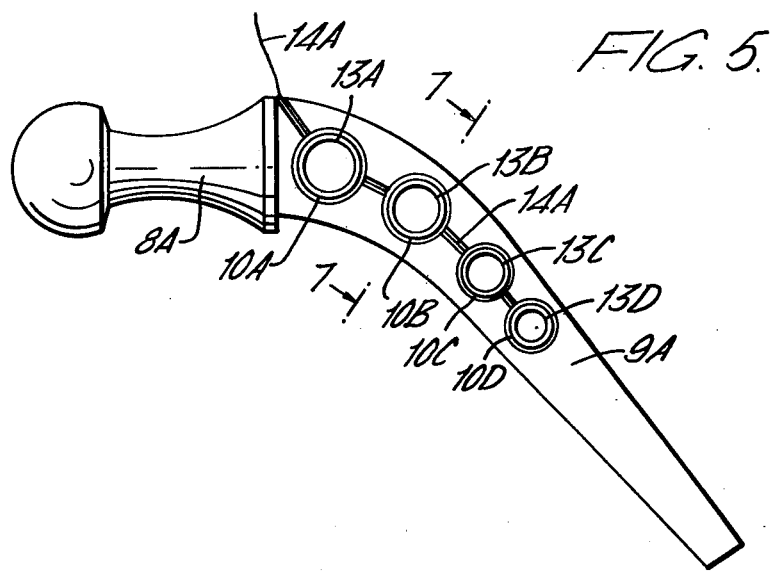
FIG. 5 is a view similar to FIG. 1 of another hip joint prosthesis according to the invention.
Figure 6:
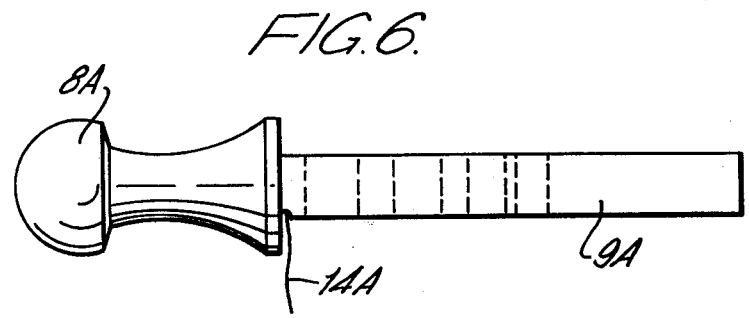
FIG. 6 is a plan view of the prosthesis of FIG. 5.
Figure 7:
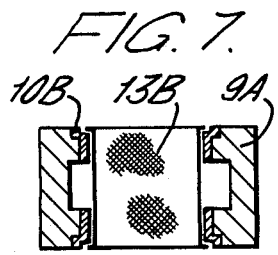
FIG. 7 is a sectional view taken on line 7—7 of FIG. 5 drawn to a larger scale.

The embodiment of FIGS. 5 and 7 also comprises a core comprising a head 8A and shaft 9A corresponding to components 8 and 9 of the above described embodiment.

In this case however a plurality of tubular wire mesh electrodes 13A, 13B, 13C and 13D are provided disposed within holes extending through the shaft 9A.

The electrodes are respectively insulated from the shaft by insulatory sleeves 10A, 10B, 10C and 10D, and each electrode may be held in place by virtue of its ends being swaged over into circumferential recesses in the ends of each sleeve.

The several electrodes are connected together and to a stimulator by means of an insulated lead 14A lodged in grooves in the surface of the shaft 9A.

In other embodiments of the invention adhesion to nonhollow bones may be obtained by suitably shaping the core and electrode to conform to the bone surface.

We claim:

1. A bone prosthesis comprising a core, said core including a head and a shaft, said shaft defining a hole pierced therein, a keying electrode substantially lining the surface of said hole and an insulating layer disposed between the core and electrode securing each to each whereby said electrode includes key formations into which bone may grow for locking engagement therewith.

2. A prosthesis according to claim 1 wherein the electrode is a wire mesh.

* * * * *